United States Patent
Yamaguchi et al.

(10) Patent No.: US 6,781,016 B2
(45) Date of Patent: Aug. 24, 2004

(54) PROCESS FOR THE PREPARATION OF ALICYCLIC KETONES AND AN ALKYL-SUBSTITUTED ALICYCLIC ESTERS

(75) Inventors: Masao Yamaguchi, Tokuyama (JP); Hiromasa Yamamoto, Tokuyama (JP); Hideki Kikuchi, Tokuyama (JP); Yoshihiro Hirota, Tokuyama (JP); Atsushi Kadokura, Tokuyama (JP); Takashi Matsumura, Tokuyama (JP)

(73) Assignee: Tokuyama Corporation, Yamaguchi-ken (JP)

( * ) Notice: Subject to any disclaimer, the term of this patent is extended or adjusted under 35 U.S.C. 154(b) by 113 days.

(21) Appl. No.: 10/258,796

(22) PCT Filed: Apr. 26, 2001

(86) PCT No.: PCT/JP01/03631

§ 371 (c)(1),
(2), (4) Date: Oct. 28, 2002

(87) PCT Pub. No.: WO01/83419

PCT Pub. Date: Nov. 8, 2001

(65) Prior Publication Data

US 2003/0109747 A1 Jun. 12, 2003

(51) Int. Cl.$^7$ .............................................. C07C 45/00
(52) U.S. Cl. ....................................................... 568/338
(58) Field of Search ......................................... 568/338

(56) References Cited

U.S. PATENT DOCUMENTS 3,433,837 A    3/1969 Geluk

FOREIGN PATENT DOCUMENTS

| EP | 0 878 234 A2 | 11/1998 |
|---|---|---|
| JP | 10-182552 A | 7/1998 |
| JP | 10-309469 A | 11/1998 |
| JP | 11-189564 A | 7/1999 |

OTHER PUBLICATIONS

Geluk et al, Tetrahedron, Hydride Transfer Reactions of the Adamantyl Cation–1. A New and Convenient Synthesis of Adamantanone, 1968, 24, pp. 5361–5368.*
Geluk et al, Tetrahedron, Hydride Transfer Reactions of the Adamantyl Cation–II. Synthesis of 1,3– and 1,4–Disubstituted Adamantanes, 1968, 24, pp. 5369–5377.*
H. W. Geluk et al.; Organic Synthesis, vol. 53, pp. 8–12, (1973).
Geluk et al., Org. Synth., vol. 53, pp. 8–12 (1973).

* cited by examiner

*Primary Examiner*—Johann Richter
*Assistant Examiner*—Paul A. Zucker
(74) *Attorney, Agent, or Firm*—Birch, Stewart, Kolasch & Birch, LLP

(57) ABSTRACT

A high-purity alicyclic ketone which is a raw material for an alkyl-substituted alicyclic ester such as an alkyl adamantyl ester compound which is useful as a resist raw material can be obtained by a simple operation such as extraction without a special purification step such as distillation or recrystallization. In this process, when an alicyclic hydrocarbon is oxidized with concentrated sulfuric acid or fuming sulfuric acid, the reaction solution after oxidation is poured into water and a solid is extracted with an organic solvent, the concentration of sulfuric acid in the water layer at the time of extraction is adjusted to 60 to 90 wt % to carry out extraction so as to obtain an alicyclic ketone.

2 Claims, No Drawings

PROCESS FOR THE PREPARATION OF ALICYCLIC KETONES AND AN ALKYL-SUBSTITUTED ALICYCLIC ESTERS

This application is the national phase under 35 U.S.C. § 371 of PCT International Application No. PCT/JP01/03631 which has an International filing date of Apr. 26, 2001, which designated the United States of America.

FIELD OF THE INVENTION

The present invention relates to processes for producing an alicyclic ketone and an alkyl-substituted alicyclic ester. More specifically, it relates to a process for producing an alicyclic ketone such as adamantanone and a process for producing an alkyl-substituted alicyclic ester from an alicyclic ketone obtained by the above process.

DESCRIPTION OF THE PRIOR ART

An alkyl-substituted alicyclic ester is a useful compound as a raw material for electronic materials and an intermediate for medicines and agricultural chemicals. For example, it is reported that a resist obtained from an alkyladamantyl ester which is an alkyl-substituted alicyclic ester has high resistance to dry etching in a semiconductor production process (JP-A 5-265212) (the term "JP-A" as used herein means an "unexamined published Japanese patent application") and attracts attention as a potential resist material for semiconductors.

An alicyclic ketone such as adamantanone is an important compound as a raw material for the above alkyl-substituted alicyclic ester and required to have high purity from its application fields.

Since a competition is becoming keen in the field of electronic materials and a great reduction in production cost is strongly desired, it is extremely important to obtain a high-purity product from an inexpensive raw material by a simple method. For example, a process for obtaining high-purity adamantanone directly and easily from adamantane without using a derivative such as adamantanol is desired in the production of adamantanone.

As means of producing adamantanone from adamantane, there has been known a process in which adamantane is oxidized using hydroxyphthalimide as a catalyst (JP-A 10-309469). However, the production process is not satisfactory because the yield of adamantanone is low at about 30%.

There has also been known a process for obtaining adamantanone at a relatively high yield by oxidizing adamantane with concentrated sulfuric acid and then purifying oxidized adamantane by steam distillation (Organic Synthesis, vol. 53. pp. 8, 1973). In this process, an object can be obtained at a relatively high yield of 47 to 48%. However, this process needs a complicated purification step, that is, steam distillation. It is also reported that specific reaction conditions are employed to improve the reaction yield of the process in which adamantane is oxidized with sulfuric acid (JP-A 11-189564).

Although a process for producing adamantanone by oxidizing adamantane with concentrated sulfuric acid or fuming sulfuric acid (to be referred to as "concentrated sulfuric acid process" hereinafter) is a very promising process because a high yield is expected and an inexpensive raw material is used, a process for obtaining a high-purity product with ease has yet to be established.

SUMMARY OF THE INVENTION

It is an object of the present invention to provide a process for producing such a high purity alicyclic ketone that a purification step is substantially unnecessary by a simple extraction operation in the above concentrated sulfuric acid process.

It is another object of the present invention to provide the above method in which the alicyclic ketone is adamantanone.

It is still another object of the present invention to provide a process for producing a useful alkyl-substituted alicyclic ester from a high-purity alicyclic ketone obtained by the above method.

Other objects and advantages of the present invention will be obvious from the following description.

According to the present invention, firstly, the above objects and advantages of the present invention are attained by a process for producing an alicyclic ketone, comprising the steps of:

oxidizing an alicyclic hydrocarbon with concentrated sulfuric acid or fuming sulfuric acid to obtain a mixture containing an alicyclic ketone and concentrated sulfuric acid or fuming sulfuric acid;

mixing the obtained mixture with water and an organic solvent;

separating an organic layer containing the alicyclic ketone from a water layer; and recovering the alicyclic ketone from the separated organic layer, wherein the concentration of sulfuric acid in the water layer is adjusted to 60 to 90 wt % when the organic layer is to be separated.

According to the present invention, secondly, the above objects and advantages of the present invention are attained by a process for producing an alkyl-substituted alicyclic ester, comprising the steps of:

reacting an alicyclic ketone obtained by the above process of the present invention with at least one alkylating reagent selected from an alkyl lithium, Grignard reagent and a combination of a haloalkyl compound and metal lithium to obtain an alkyl-substituted alicyclic alkoxide; and reacting the obtained alkyl-substituted alicyclic alkoxide with an acid halide to produce an alkyl-substituted alicyclic ester.

THE PREFERRED EMBODIMENT OF THE INVENTION

In the process for producing an alicyclic ketone of the present invention, an alicyclic hydrocarbon is first oxidized with concentrated sulfuric acid or fuming sulfuric acid to obtain a mixture containing an alicyclic ketone and concentrated sulfuric acid or fuming sulfuric acid.

Any alicyclic hydrocarbon may be used as a raw material compound if it is a cyclic hydrocarbon and compound having no unsaturated bond. However, it is preferably a saturated alicyclic hydrocarbon having high symmetry because the position to be oxidized is limited and a single alicyclic ketone is easily obtained. Preferred examples of the alicyclic hydrocarbon include adamantane and cyclohexane. Out of these compounds, adamantane is most preferred because an oxidation reaction proceeds selectively and efficiently, an alicyclic ketone obtained therefrom is useful as an intermediate for medicines, agricultural chemicals and electronic materials, and high purity is desired.

The process for obtaining an alicyclic ketone by contacting the above alicyclic hydrocarbon with concentrated sulfuric acid or fuming sulfuric acid to oxidize the alicyclic hydrocarbon is identical to the conventional concentrated sulfuric acid process for producing an alicyclic ketone compound. Therefore, the process described at page 8 of Organic Synthesis vol. 53, 1973, the process disclosed by JP-A 11-189564 and known processes can be applied without restriction.

The oxidation of the alicyclic hydrocarbon can be advantageously carried out by mixing and stirring an alicyclic hydrocarbon and concentrated sulfuric acid in the absence of a solvent and heating. The concentration of concentrated sulfuric acid at this point is preferably 96 wt % or more and fuming sulfuric acid may also be used. The amount of the alicyclic hydrocarbon is not particularly limited but preferably 0.1 to 5 mols based on 1 kg of the concentrated sulfuric acid or fuming sulfuric acid. As for the reaction temperature and the reaction time which differ according to the type of the alicyclic hydrocarbon to be oxidized, the alicyclic hydrocarbon is preferably reacted at 50 to 100° C. for 0.5 to 48 hours. More preferably, the temperature is elevated by checking the proceeding of the reaction.

The reaction temperature may be changed in two stages. For example, the first stage of the reaction is carried out at 50 to 60° C. and then the second stage of the reaction is carried out at 60 to 100° C. The formation of a resin-like substance in particular can be suppressed by this two-stage reaction.

A reaction solution which is a mixture containing an alicyclic ketone (object) having a —C(=O)— group formed by oxidizing a —CH$_2$— group contained in the alicyclic hydrocarbon and concentrated sulfuric acid or fuming sulfuric acid can be obtained by the above reaction.

In the present invention, after the thus obtained reaction solution, water and an organic solvent are mixed together, a water layer and an organic layer containing an alicyclic ketone compound are separated from each other. The concentration of sulfuric acid in the water layer (defined as wt % of sulfuric acid based on the total weight of water and sulfuric acid) at this point is controlled to 60 to 90 wt %. When the concentration of sulfuric acid at the time of separation is lower than 60 wt %, impurities are contained in the organic layer and a high-purity object cannot be therefore obtained by an extraction operation alone. When the above concentration of sulfuric acid is higher than 90 wt %, it is substantially impossible to extract the object with an organic solvent. By controlling the concentration of sulfuric acid to 90 wt % or less, the object can be recovered. The concentration of sulfuric acid in the water layer is preferably 70 to 80 wt % from the viewpoints of the purity and yield of the obtained object.

In the conventional production process using concentrated sulfuric acid, in general, after the reaction product is added to an excessive amount of water in consideration of heat generated at the time of mixing water, the object is extracted with an organic solvent. When this process is employed, the concentration of sulfuric acid in the water layer at the time of extraction is low (generally about 40 wt %).

In contrast to this, the concentration of sulfuric acid in the water layer at the time of extraction is adjusted to the above very high specific range in the present invention, whereby the object contained in the reaction solution can be selectively extracted with the result that the high-purity object can be obtained by a simple extraction operation without a special purification step such as distillation or recrystallization. Although the reason that the above excellent effect is obtained is not made clear, it is considered that the object differs from impurities in solubility in a specific concentration of sulfuric acid.

The method of mixing the reaction solution with water and the organic solvent is not particularly limited. However, it is preferred from the viewpoints of safety and operation efficiency that the reaction solution be poured into water and/or ice (to be simply referred to as "water and the like" hereinafter) and then the organic solvent be added to and mixed with the resulting solution. The total amount of water and the like used is preferably such that the concentration of sulfuric acid in the water layer is 60 to 90 wt %, specifically 70 to 80 wt % when ice is wholly molten because the concentration of sulfuric acid does not need to be adjusted later. It is also possible as a matter of course to use water and the like more than the above preferred amount and add concentrated sulfuric acid so as to adjust the concentration of sulfuric acid in the water layer to 60 to 90 wt %.

Any organic solvent may be used for extraction in the present invention if it does not react with sulfuric acid, dissolves the alicyclic ketone of interest and is insoluble in sulfuric acid. A suitable organic solvent may be selected from among known organic solvents in consideration of the solubility of the alicyclic ketone to be extracted. The organic solvent which can be suitably used in the present invention is an aliphatic hydrocarbon such as hexane or cyclohexane; aromatic hydrocarbon such as toluene or xylene; hydrogenated hydrocarbon such as dichloromethane, chloroform or chlorobenzene; ether such as diethyl ether or anisole; or ester such as ethyl acetate or butyl acetate.

The amount of the organic solvent is not particularly limited if it dissolves all the aliphatic ketone of interest. However, it is preferred such that the amount of the aliphatic ketone is 25 to 75% of its saturated concentration in the extraction solvent in consideration of operation efficiency and time and labor required for the drying and removal of the solvent in the subsequent step.

After the reaction solution is poured into water and the like, the above organic solvent is added, stirred well and left to stand to separate and recover the organic layer from the water layer by a separation operation, the separated organic layer is washed with water or an aqueous solution of a neutral salt as required, and dried by azeotropic dehydration or using a desiccant such as sodium sulfate or calcium chloride, the desiccant is removed, and then the solvent is removed to obtain a high-purity alicyclic ketone.

The thus obtained high-purity alicyclic ketone can be suitably used as a raw material for synthesizing an alkyl-substituted alicyclic ester.

Therefore, according to the present invention, there is also provided a process for producing an alkyl-substituted alicyclic ester from a high-purity alicyclic ketone.

In this process, an alkyl-substituted alicyclic alkoxide is first obtained by reacting the alicyclic ketone with at least one alkylating reagent selected from the group consisting of (1) an alkyl lithium, (2) a Grignard reagent and (3) a combination of a haloalkyl compound and metal lithium.

Compounds suitably used as the alkylating reagent include alkyl lithiums such as methyl lithium, ethyl lithium and butyl lithium, Grignard reagents such as methyl magnesium bromide and ethyl magnesium chloride, and haloalkyls such as methyl iodide and ethyl bromide.

The above reaction process is not particularly limited. For example, it is preferably carried out by reacting an almost equimolar amount or a little excessive amount of the alkylating reagent with the alicyclic ketone in an organic solvent.

Any known organic solvent may be used as the solvent if it does not react with the alkylating agent. Preferred examples of the organic solvent include ether-based solvents such as diethyl ether, tetrahydrofuran and ethylene glycol dimethyl ether; and hydrocarbon-based solvents such as hexane and toluene.

The above reaction conditions are not particularly limited but the amount of the alkylating reagent is preferably 0.9 to 1.5 mols, particularly preferably 1.0 to 1.3 mols based on 1 mol of the aliphatic ketone. The amounts of the haloalkyl compound and metal lithium are 0.8 to 2.0 mols and 1.5 to 2.5 grams-atom, particularly preferably 1.0 to 1.2 mols and 1.8 to 2.0 grams-atom based on 1 mol of the alicyclic ketone, respectively, when the above combination (3) of a haloalkyl compound and metal lithium is used as the alkylating reagent. The reaction temperature is not particularly limited and may be suitably determined according to the type of the alkylating reagent. When the above alkylating reagent (1) or (2) is used, it is preferably 20 to 80° C. When the alkylating reagent (3) is used and an iodide is used as the haloalkyl, it is preferably −80 to 20° C., and when a bromide or chloride is used, it is preferably 0 to 100° C. The reaction time which differs according to the type of the alkylating reagent is generally 0.5 to 24 hours.

The thus obtained alkyl-substituted alicyclic alkoxide is reacted with an acid halide without being isolated. The acid halide used may be an acid halide having a structure corresponding to the type of an alkyl-substituted alicyclic ester of interest. Preferred examples of the acid halide include acetyl chloride, methacrylic acid chloride, acrylic acid chloride and benzoyl chloride.

The method of reacting the alkyl-substituted alicyclic alkoxide with the acid halide is not particularly limited and any known method may be used. For example, both are preferably mixed together in the presence of a solvent. The amount of the acid halide is preferably 0.9 to 2.0 mols, particularly preferably 1.0 to 1.3 mols based on 1 mol of the alkyl-substituted alicyclic alkoxide. When an excessive amount of the acid halide is used, 1 mol or more of a tertiary amine may be added based on 1 mol of the acid halide. Particularly when the alkyl-substituted alicyclic ester of interest is instable to an acid, such an amount of a tertiary amine is preferably added. The tertiary amine is not particularly limited but triethylamine, pyridine, dimethylaminopyridine and diazabicyclo[2.2.2.]octane may be used. The reaction temperature and the reaction time which differ according to the type of the acid halide are generally 20 to 100° C. and 0.5 to 24 hours, respectively.

The thus obtained alkyl-substituted alicyclic ester is subjected to a post-treatment consisting of rinsing, drying and solvent removal, and can be isolated by a general purification technique such as column chromatography, distillation or recrystallization.

EXAMPLES

The following examples are provided for the purpose of further illustrating the present invention but are in no way to be taken as limiting.

Example 1

120 ml of 30% fuming sulfuric acid was added to 480 ml of 96% sulfuric acid to prepare 98% sulfuric acid, and 100 g of adamantane was added to this sulfuric acid and heated at 70° C. while they were violently stirred. The temperature was then raised to 80° C. over 2 hours and the obtained reaction solution was stirred at 82° C. for 1 hour. Thereafter, the reaction solution was cooled, 250 g of the reaction solution was poured into 65.6 g of water to ensure that the concentration of sulfuric acid in the water layer should be 72 wt %, and the organic layer was extracted with 250 ml of methylene chloride two times. The organic layer was washed with a 10% aqueous solution of sodium hydroxide and brine sequentially and dried with magnesium sulfate, and methylene chloride was distilled off to obtain 15.2 g of a solid. When the obtained solid was analyzed by gas chromatography using dodecane as an internal standard, the purity of 2-adamantanone was 96%.

Example 2

14.6 g of a solid was obtained in the same manner as in Example 1 except that 250 g of the reaction solution obtained in Example 1 was poured into 43.2 g of water to ensure that the concentration of sulfuric acid in the water layer should be 78 wt %. The purity of the obtained 2-adamantanone was 98%.

Comparative Example 1

When 250 g of a reaction solution obtained in the same manner as in Example 1 was poured into 135.7 g of water to ensure that the concentration of sulfuric acid in the water layer should be 58 wt %, a large amount of tar separated out. Thereafter, extraction, washing and drying were carried out in the same manner as in Example 1, and the solvent was distilled off to obtain 21.8 g of a solid. When the purity of the obtained 2-adamantanone was determined by the internal standard method, it was 67%.

Comparative Example 2

A solid was extracted twice with 250 ml of methylene chloride without adding water to 250 g of the reaction solution obtained in Comparative Example 1, and then washing, drying and solvent removal were carried out in the same manner as in Example 1. However, 2-adamantanone was hardly obtained.

Examples 3 and 4

Solids were obtained in the same manner as in Example 1 except that water was mixed with 250 g of a reaction solution obtained in the same manner as in Example 1 to ensure that the concentration of sulfuric acid in the water layer should be 67 wt % (Example 3) and 85 wt % (Example 4). The weight and purity of the obtained 2-adamantanone were 15.5 g and 97% (Example 3) and 12.2 g and 98% (Example 4).

In Example 4, the yield of 2-adamantanone was a little low. However, since easy acquisition of a high-purity product is prior to yield when equipment and labor required for purification are taken into consideration, such a reduction in yield does not negate the value of the present invention.

Examples 5 to 7

100 g of adamantane was suspended in 1 kg of 98% concentrated sulfuric acid and stirred at 50° C. for 6 hours and further at 60° C. for 23 hours, the proceeding of a reaction was checked by gas chromatography, and the reaction solution was cooled. 20 g of this solution was added dropwise to a dispersion of 130 g of methylene chloride and an amount shown in Table 1 of water under cooling to adjust the concentration of sulfuric acid to a value shown in Table 1, and the obtained solution was left to stand to separate a methylene chloride layer. The sulfuric acid layer was extracted with 130 g of methylene chloride again and washed with a 10% aqueous solution of sodium hydroxide and 20% brine together with the organic layer. Methylene chloride was distilled off and the weight and purity of the solid were measured. The results are shown in Table 1.

TABLE 1

|  | amount of water (g) | concentration of sulfuric acid (wt %) | yield (g) | purity (%) |
| --- | --- | --- | --- | --- |
| Ex. 5 | 6.8 | 70 | 1.4 | 97 |
| Ex. 6 | 5.0 | 75 | 2.1 | 98 |
| Ex. 7 | 3.4 | 80 | 1.7 | 98 |

Ex.: Example

Example 8

Comparative Example 3

36 g of fuming sulfuric acid (containing 25% of sulfuric trioxide) (9 g or 0.11 mol of sulfur trioxide) was cooled to 10° C. or less, and 10 g (0.07 mol) of adamantane was added and stirred at 10° C. or less for 3 hours. The temperature was then raised to 50° C. and further to 80° C. over 4 hours. The proceeding of a reaction was checked by gas chromatography and then the obtained solution was cooled. 15 g of the solution was added dropwise to a dispersion of 150 g of methylene chloride and an amount shown in Table 2 of water under cooling to adjust the concentration of sulfuric acid to a value shown in Table 2 and stirred at room temperature for one night. Thereafter, the reaction solution was left to stand to separate the methylene chloride layer which was then washed with a 10% aqueous solution of sodium hydroxide and 20% brine. Methylene chloride was distilled off and the weight and purity of the obtained solid were measured by the internal standard method of gas chromatography. The results are shown in Table 2.

TABLE 2

|  | amount of water (g) | concentration of sulfuric acid (wt %) | yield (g) | purity (%) |
| --- | --- | --- | --- | --- |
| Ex. 8 | 4.5 | 70 | 1.6 | 98 |
| C. Ex. 3 | 10.5 | 50 | 2.3 | 54 |

Ex.: Example
C. Ex.: Comparative Example

In Example 8 and Comparative Example 3, the yield of 2-adamantanone was not so high. This is because a large amount of tar was produced due to use of fuming sulfuric acid. As understood from comparison between Example 8 and Comparative Example 3, a high-purity product can be obtained easily from a reaction solution containing impurities in large quantities.

Example 9

15 g (0.1 mol) of 2-adamantanone obtained in Example 1 was dissolved in 50 ml of tetrahydrofuran, and 100 ml (1 mol/l) of a tetrahydrofuran solution of methyl magnesium bromide prepared in advance was added dropwise to the above solution at 40° C. or less. After the proceeding of a reaction was checked by gas chromatography, 2.5 g (0.025 mol) of triethylamine and 13 g (0.125 mol) of methacrylic acid chloride were added to the reaction solution and stirred at 50° C. for 3 hours. The proceeding of the reaction was checked by gas chromatography, and then 10 ml of water was added to stop the reaction. Thereafter, tetrahydrofuran was distilled off under reduced pressure, 50 ml of heptane was added, and the obtained solid was washed with a 1N aqueous solution of ammonium chloride, a 10% aqueous solution of sodium hydroxide and ion exchange water sequentially. Thereafter, heptane was distilled off in reduced pressure to obtain 24 g of a crude product. When 1.5 g of diethylene glycol was added to this crude product to carry out vacuum distillation (92° C./0.4 mmHg), 12 g (0.51 mol, 51%) of 2-methyl-2-adamantyl methacrylate was obtained.

Example 10

15 g (0.1 mol) of 2-adamantanone obtained in Example 3 was dissolved in 50 ml of tetrahydrofuran, and 12 g (0.11 mol) of ethyl bromide was added to the resulting solution. 0.1 g of metal lithium was added to the solution each time until the total amount became 1.3 g (0.19 mol) in such a manner that the temperature of the solution should not exceed 30° C. while they were violently stirred. After the proceeding of a reaction was checked by gas chromatography and it was confirmed visually that the metal lithium disappeared, 10 g (0.1 mol) of methacrylic acid chloride was added to the reaction solution. After it was confirmed by gas chromatography that the reaction proceeded to the full, 3 ml of methanol and 3 ml of a 5% aqueous solution of sodium hydroxide were added to the reaction solution and stirred at room temperature for 1 hour to stop the reaction. Thereafter, the organic solvent was distilled off under reduced pressure, 200 ml of hexane was added, and the obtained solution was washed with a 10% aqueous solution of sodium hydroxide and 20% brine sequentially. Thereafter, hexane was distilled off under reduced pressure to obtain a crude product which was then recrystallized in isopropanol to obtain 7.2 g (0.029 mol, 29%) of 2-ethyl-2-adamantyl methacrylate.

As described above, according to the present invention, a high-purity alicyclic ketone can be easily obtained from an alicyclic hydrocarbon which is a primary raw material without a purification step which requires exclusive equipment and labor, such as distillation or recrystallization. By employing the production process of the present invention, high-purity adamantanone which is useful as an intermediate for medicines and agricultural chemicals and a raw material for electronic materials can be easily produced.

When an alkyl-substituted alicyclic ester is produced from the thus obtained alicyclic ketone, the step of purifying the above raw material alicyclic ketone can be omitted from the entire production process.

What is claimed is:

1. A process for producing an alicyclic ketone, comprising the steps of:
    oxidizing adamantane with concentrated sulfuric acid or fuming sulfuric acid to obtain a mixture containing adamantanone and concentrated sulfuric acid or fuming sulfuric acid;
    mixing the obtained mixture with water and an organic solvent;
    separating an organic layer containing adamantanone from a water layer; and
    recovering adamantanone from the separated organic layer, wherein
    the concentration of sulfuric acid in the water layer is adjusted to 60 to 90 wt % when the organic layer is to be separated.

2. A process for producing an alkyl-substituted alicyclic ester, comprising the steps of:
    reacting adamantaanone obtained by the process of claim 1 with at least one alkylating reagent selected from the group consisting of an alkyl lithium, Grignard reagent and a combination of a haloalkyl compound and metal lithium to obtain an alkyl-substituted alicyclic alkoxide; and
    reacting the obtained alkyl-substituted alicyclic alkoxide with an acid halide to produce an alkyl-substituted alicyclic ester.

* * * * *

UNITED STATES PATENT AND TRADEMARK OFFICE
CERTIFICATE OF CORRECTION

PATENT NO. : 6,781,016 B2
DATED : August 24, 2004
INVENTOR(S) : Yamaguchi Masao et al.

It is certified that error appears in the above-identified patent and that said Letters Patent is hereby corrected as shown below:

<u>Title page,</u>
Item [30], Foreign Application Priority Data, should read as follows:
-- [30] Foreign Application Priority Data
     April 28, 2000 (JP) ..........2000-129295" --

Signed and Sealed this

Fourteenth Day of December, 2004

JON W. DUDAS
*Director of the United States Patent and Trademark Office*